(12) United States Patent
Patterson et al.

(10) Patent No.: US 8,731,653 B2
(45) Date of Patent: May 20, 2014

(54) MONITOR OF HEART FAILURE USING BIOIMPEDANCE

(75) Inventors: Robert Patterson, Minneapolis, MN (US); Fei Yang, Saint Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 354 days.

(21) Appl. No.: 13/122,664

(22) PCT Filed: Oct. 9, 2009

(86) PCT No.: PCT/US2009/060223
§ 371 (c)(1),
(2), (4) Date: Jun. 20, 2011

(87) PCT Pub. No.: WO2010/042855
PCT Pub. Date: Apr. 15, 2010

(65) Prior Publication Data
US 2011/0245712 A1    Oct. 6, 2011

Related U.S. Application Data

(60) Provisional application No. 61/104,631, filed on Oct. 10, 2008.

(51) Int. Cl.
*A61B 5/053* (2006.01)
*A61B 5/00* (2006.01)
*A61N 1/365* (2006.01)

(52) U.S. Cl.
CPC ............ *A61B 5/0535* (2013.01); *A61B 5/4878* (2013.01); *A61N 1/36521* (2013.01)
USPC ......................................................... 600/547

(58) Field of Classification Search
USPC ........................................................ 600/547
See application file for complete search history.

(56) References Cited

U.S. PATENT DOCUMENTS

| | | | |
|---|---|---|---|
| 5,876,353 | A | 3/1999 | Riff |
| 5,957,861 | A | 9/1999 | Combs et al. |
| 6,104,949 | A | 8/2000 | Crick et al. |

(Continued)

FOREIGN PATENT DOCUMENTS

| | | |
|---|---|---|
| CN | 101163443 A | 4/2008 |
| EP | 0985429 B1 | 12/2004 |
| WO | WO99/43385 A1 | 9/1999 |
| WO | WO 2005/037367 | 4/2005 |

OTHER PUBLICATIONS

Chinese Search Report; Oct. 23, 2012; China; 200980145628.8; 4 pages.

(Continued)

*Primary Examiner* — Sean Dougherty
*Assistant Examiner* — Michael C Stout
(74) *Attorney, Agent, or Firm* — Fish & Richardson P.C.

(57) ABSTRACT

In a method of monitoring pulmonary edema in a human being, an electrical current is injected between a first electrode located in or around a heart and a housing of a medical device implanted in a chest region. A voltage potential is measured between a second electrode in a superior vena cava and a third electrode in the superior vena cava, where the voltage potential is created by the electrical current. Pulmonary edema is assessed based on an impedance value calculated from the electrical current and the voltage potential and a stored edema threshold impedance value.

20 Claims, 11 Drawing Sheets

(56) References Cited

U.S. PATENT DOCUMENTS

| | | |
|---|---|---|
| 6,438,408 B1 | 8/2002 | Mulligan et al. |
| 6,473,640 B1 | 10/2002 | Erlebacher |
| 6,512,949 B1 | 1/2003 | Combs et al. |
| 6,595,927 B2 | 7/2003 | Crick et al. |
| 6,931,272 B2 | 8/2005 | Burnes |
| 7,177,681 B2 | 2/2007 | Zhu et al. |
| 7,184,821 B2 | 2/2007 | Belalcazar et al. |
| 7,272,443 B2 | 9/2007 | Min et al. |
| 7,313,434 B2 | 12/2007 | Belalcazar et al. |
| 7,447,543 B2 * | 11/2008 | Belalcazar et al. ........... 600/547 |
| 8,428,718 B2 * | 4/2013 | Stadler et al. .................. 607/17 |
| 2005/0124908 A1 | 6/2005 | Belalcazar et al. |
| 2005/0267381 A1 | 12/2005 | Benditt et al. |
| 2006/0064029 A1 | 3/2006 | Arad |
| 2006/0184060 A1 * | 8/2006 | Belalcazar et al. ........... 600/547 |
| 2007/0203420 A1 | 8/2007 | Belalcazar et al. |
| 2008/0091114 A1 | 4/2008 | Min et al. |
| 2008/0125826 A1 * | 5/2008 | Belalcazar et al. ............. 607/17 |
| 2009/0069708 A1 * | 3/2009 | Hatlestad et al. ............. 600/547 |
| 2012/0053470 A1 * | 3/2012 | Wong et al. ................... 600/508 |

OTHER PUBLICATIONS

Authorized Officer Lee W. Young, International Search Report & Written Opinion for PCT/US09/60223, mailed Dec. 10, 2010, 8 pages.

Authorized Officer Beate Giffo-Schmitt, International Search Report for PCT/US09/60223, mailed Apr. 21, 2010, 8 pages.

* cited by examiner

MONITOR OF HEART FAILURE USING BIOIMPEDANCE

CROSS-REFERENCE TO RELATED APPLICATIONS

This application is a National Stage application under 35 U.S.C. §371 of International Application No. PCT/US2009/060223, having an International Filing Date of Oct. 9, 2009, which claims priority to U.S. Provisional Application Ser. No. 61/104,631, filed on Oct. 10, 2008, and entitled "Improved Monitor Of Heart Failure Using Bioimpedance," both of which are incorporated herein by reference.

TECHNICAL FIELD

The description relates to impedance monitoring in a living being for the detection of pulmonary edema and thoracic congestion.

BACKGROUND

Pulmonary edema is a serious medical condition caused by an excess accumulation of fluid within a patient's lungs. Pulmonary edema can be an indicator of cardiac-related diseases, such as congestive heart failure. Good management of pulmonary edema is desirable because it may allow timely therapeutic interventions, and avoid hospitalization and its costs.

It is possible to detect fluid in the lungs by making an electrical impedance measurement across the lungs. The more fluid there is in the lungs, the lower the impedance. One known way this may be done is by using an implantable medical device such as a pacemaker or defibrillator implanted in the chest area of the patient. An electrical impedance measurement is conventionally made between right ventricular chamber electrodes connected to the implanted device, and another electrode at the implanted device itself; thus, the impedance measurement samples thoracic tissues, including the lungs. This configuration may also be used to measure impedance for determining a patient's respiration rate, which may subsequently be used to aid in the regulation and issuance of pacing stimuli to the heart. For instance, a patient whose respiration rate increases due to exercise, for example, may require pacing stimuli to be delivered at a faster rate.

SUMMARY

In a first general aspect, a method of monitoring pulmonary edema in a human being includes injecting an electrical current between a first electrode located in or around a heart and a housing of a medical device implanted in a chest region. The method also includes measuring a voltage potential between a second electrode in a superior vena cava and a third electrode in the superior vena cava, where the voltage potential is created by the electrical current. The method further includes assessing pulmonary edema based on an impedance value calculated from the electrical current and the voltage potential and a stored edema threshold impedance value.

Various implementations can include one or more of the following. The injected electrical current may be a cardiac pacing pulse configured to initiate a cardiac cycle, or may be configured such that a cardiac cycle is not initiated in response to injection of the electrical current. The second electrode and the third electrode may positioned on a lead, a distal end of which may be located in a right ventricle. A second voltage potential may be measured between a fourth electrode in the vena cava and either the second electrode or the third electrode, and a second impedance value based on the electrical current and the second voltage potential may be calculated to assess pulmonary edema. Heart enlargement may be assessed based on the calculated impedance values. Relative contributions to impedance changes attributable to pulmonary edema and heart enlargement may be determined by solving a system equations using the calculated impedance values and predetermined coefficients. Two of the second electrode, third electrode and fourth electrode may be positioned on a first lead and the remaining electrode may be positioned on a second lead, or each of the second, third and fourth electrodes may be positioned on a single lead. The current injection, voltage measurement, and impedance value calculation may be repeated on a periodic basis and the assessment of pulmonary edema may include assessing a change in edema based on two or more of the calculated impedance values.

In a second general aspect, a method of monitoring pulmonary edema in a human being includes injecting an electrical current between a first electrode located in a right ventricle of a heart and a housing of a medical device implanted in a chest region. The method also includes measuring a voltage potential between a second electrode in a superior vena cava and a third electrode in the superior vena cava, where the voltage potential is created by the electrical current. The method further includes assessing pulmonary edema based on an impedance value calculated from the electrical current and the voltage potential and a stored edema threshold impedance value.

In a third general aspect, a method of monitoring pulmonary edema in a human being includes injecting an electrical current between a first electrode located in a coronary vein of a left ventricle of a heart and a housing of a medical device implanted in a chest region. The method also includes measuring a voltage potential between a second electrode in a superior vena cava and a third electrode in the superior vena cava, where the voltage potential is created by the electrical current. The method further includes assessing pulmonary edema based on an impedance value calculated from the electrical current and the voltage potential and a stored edema threshold impedance value.

In a fourth general aspect, an implantable medical device includes a housing for the implantable device sized for implantation in a chest region of a patient and comprising a housing electrode. The device also includes a lead port into which a proximal end of a lead is connectable, the lead having first, second, and third conductors that are insulated from one another and that extend from the proximal end of the lead to corresponding first, second, and third electrodes, the third electrode positioned near a distal end of the lead for location in or around a heart, and the first and second electrodes positioned on the lead for location in a superior vena cava. The device also includes an electrical impedance measurement circuit electrically connected to the lead port and the housing electrode. The circuit includes a current generator, a voltage amplifier and a control module, where the current generator is designed to inject an electrical current between the third electrode located in or around the heart and the housing electrode, the voltage amplifier is designed to measure a voltage potential between the first and second electrodes located in the superior vena cava, where the voltage potential is created by the electrical current, and the control module is designed to assess pulmonary edema based on an impedance value calculated from the electrical current and the voltage potential and a stored edema threshold impedance value.

Various implementations may include one or more of the following. The injected electrical current may be a cardiac pacing pulse configured to initiate a cardiac cycle, or may be configured such that a cardiac cycle is not initiated in response to injection of the electrical current. The current injection, voltage measurement, and impedance value calculation may be repeated on a periodic basis and the assessing pulmonary edema may include assessing a change in edema based on two or more of the calculated impedance values. The control module may be further designed to assess heart enlargement based on the calculated impedance values. Relative contributions to impedance changes attributable to pulmonary edema and heart enlargement may be determined by solving a system equations using the calculated impedance values and predetermined coefficients.

The details of one or more implementations are set forth in the accompanying drawings and the description below. Other features and advantages will be apparent from the description and drawings, as well as from the claims.

DESCRIPTION OF DRAWINGS

This document describes these and other aspects in detail with reference to the following drawings.

Like reference symbols in the various drawings indicate like elements.

DETAILED DESCRIPTION OF ILLUSTRATIVE EMBODIMENTS

Figure 1:
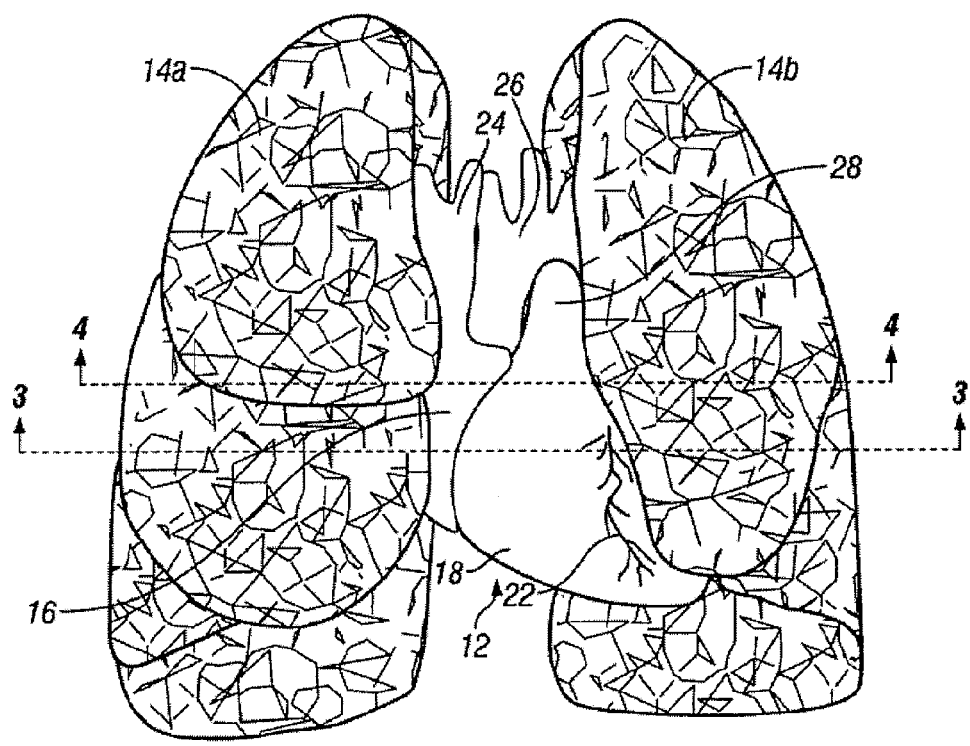
FIG. 1 is a perspective diagram of a human heart and lungs.

Before discussing the medical device used to detect pulmonary edema or thoracic congestion, it will be helpful to discuss first the relative positioning of a human heart and lungs, and the phases of a cardiac cycle. FIG. 1 is an illustrative partial front view of a human heart 12 positioned between a right lung 14a and a left lung 14b.

A superior vena cava 24 receives deoxygenated blood from a body's upper extremities and thorax, and empties the blood into a right atrial chamber 16, referred to as the right atrium. A left atrial chamber (left atrium, not shown in FIG. 1) conversely receives oxygenated blood from the lungs 14. The atria (right atrium 16 and left atrium) then contract and force blood into a right ventricular chamber 18 (right ventricle), and left ventricular chamber (left ventricle, covered by the left lung 14b in FIG. 1), respectively. After this atrial contraction, the cardiac cycle reaches the end of diastole, with the ventricles dilated and filled with blood. The right ventricle 18 and left ventricle serve as blood pumps to pump blood away from the heart 12. The right ventricle 18 pumps deoxygenated blood to the lungs 14 through a pulmonary artery 28. Within the lungs 14, the blood becomes re-oxygenated and is then moved to the left atrium, as discussed above. The left ventricle, having received oxygenated blood from the lungs 14 through the left atrium, pumps the oxygenated blood to the body through an aorta 26, a large artery leaving the left ventricle. This second part of the cardiac cycle may be referred to as systole, because the ventricles contract as the blood is pumped therefrom.

In FIG. 1, a section of the aorta 26 known as the aortic arch is shown. An inter-ventricular vein 22, which runs substantially vertically in FIG. 1, marks a division between the right ventricle 18 and left ventricle. As seen in FIG. 1, the lungs 14 are close to the heart 12, the closest portions being the left ventricle and right atrium 16. The right ventricle 18, in contrast, is located away from the large volume of lung tissue 14, approximately between the right lung 14a and left lung 14b on the anterior side.

Figure 2:
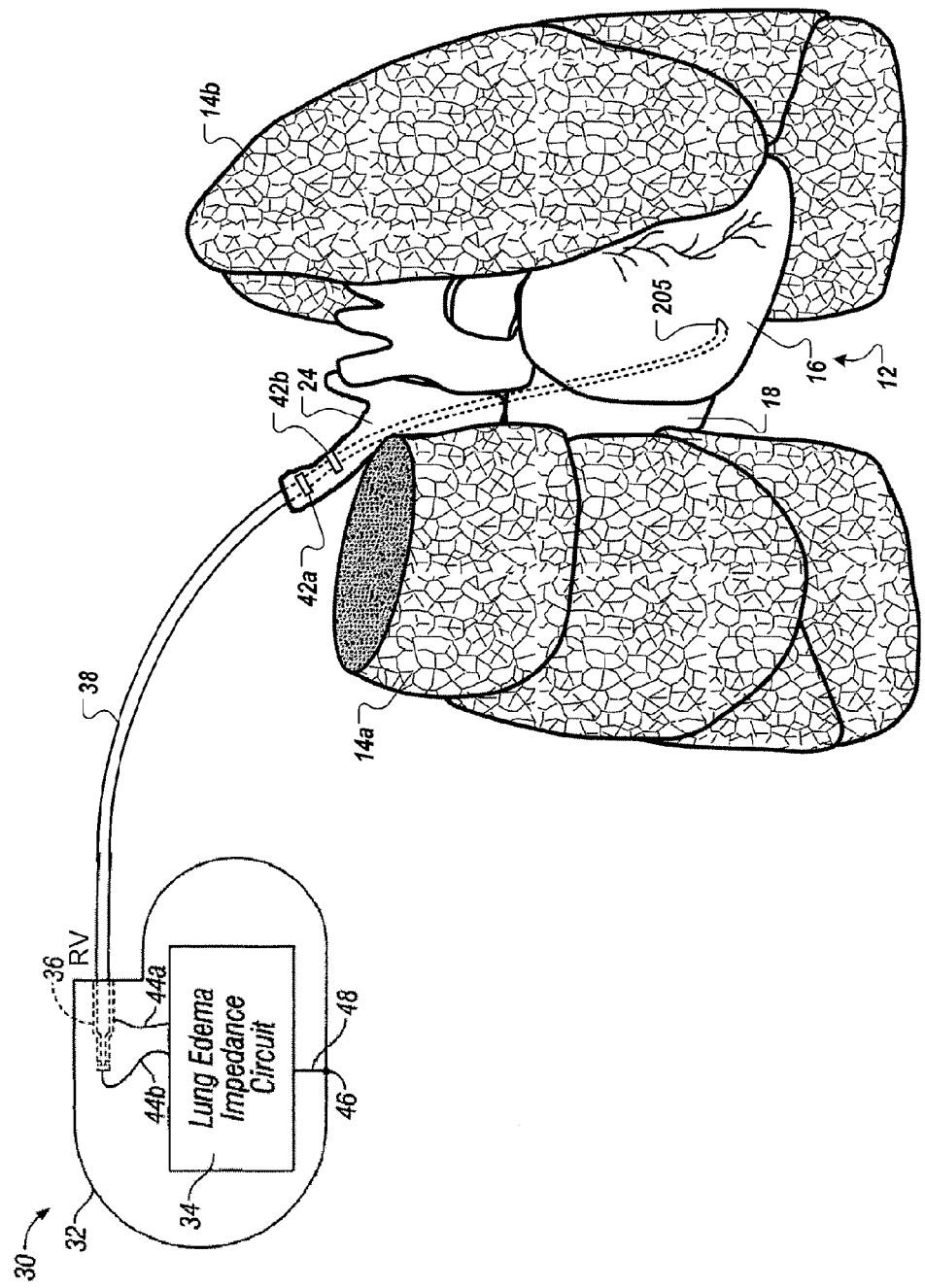
FIG. 2 is a diagram of an example implantable device in accordance with an embodiment and the heart and lungs from FIG. 1.

Referring now to FIG. 2, an illustrative view of the heart and lungs from FIG. 1 and an implantable device 30 is shown. The implantable device 30 includes a housing 32 that houses a lung edema impedance circuit 34. The lung edema impedance circuit 34 may measure lung impedance and assess pulmonary edema levels. The device 30 includes a right ventricular port 36 for attaching a right ventricular cardiac lead 38. In FIG. 2, the lead 38 is attached to the right ventricular (RV) port 36. The lead 38 may then be introduced into the venous system, down the superior vena cava 24, into the right atrium 16, through the tricuspid valve (not shown), and into the right ventricle 18 (visible in FIG. 2 because portions of the lungs 14 have been removed for display purposes).

In the depicted example, the lead 38 has two electrodes 42a, 42b, positioned within the superior vena cava, and a tip electrode 205 located in the right ventricle. The electrodes 42a, 42b are electrically connected to conductors (not shown) that run through the lead 38. When the lead 38 is attached to the port, the conductors are individually electrically connected to wires or traces within the device 30 that couple the connector port to the lung edema impedance circuit 34, thereby establishing electrical connections between the circuit 34 and the electrodes. For simplicity, two such wires 44a, 44b are representatively shown in FIG. 2, and may be representative of an appropriate number of wires (e.g., three in this example) for separately establishing connections to the electrodes on the lead (electrodes 42a, 42b, and 205 in this example). For example, the device may include a separate wire that connects the circuit 34 to a connector port for each electrode to be utilized, and this can be extended for implementations having more or fewer electrodes, such as other implementations discussed herein. Electrode 42a may be referred to as a proximal electrode, and electrode 42b may be referred to as a distal electrode because of their relative positions on the lead 38 with respect to the housing 32.

Although electrodes 42a and 42b are shown as ring electrodes located at particular locations in the superior vena cava, the electrodes 42a and 42b may be located elsewhere in the vena cava. While the lead 38 is shown in FIG. 2 with three electrodes (42a, 42b, 205), the lead 38 may include additional or fewer electrodes, and may follow a different path through the heart 12 from that shown in FIG. 2. In some implementations, the electrodes 42a, 42b can be on the same lead 38 as the current injection electrode (e.g., the tip electrode 205). In some implementations, any or all of the electrodes can be formed on different leads, as will be discussed in examples described with reference to FIG. 6.

A can electrode 46 on an exterior surface of the device housing 32 is electrically connected to the lung edema impedance circuit 34 through a wire 48 to complete a four-electrode configuration. In various embodiments, the implantable device 30 may operate by injecting an electrical current between the tip electrode 205 and the can electrode 46, for example, and a voltage may be measured between the electrodes 42a and 42b, which are located in the superior vena cava 24.

In some embodiments, the can electrode 46 may be supplemented and/or replaced with a header electrode (not shown). The header electrode may include a conductor located on an exterior surface of a header of the device 30.

In operation, the electrodes 42a, 42b detect a voltage induced by a current injected between the tip electrode 205 located in the right ventricle 18 and the can electrode 46. The difference between two voltages measured at the electrodes 42a and 42b may provide information that can be used to assess tissue impedance, for example, in the lungs, heart, and/or muscle tissues. As will be described with reference to, for example, to FIG. 8A, measured voltage in the superior vena cava 24 responsive to a known injected current can be used to measure, assess, and/or estimate impedance of other tissues through which the injected current may flow. In various embodiments, two or more voltage-sensing electrodes may be positioned within the vena cava to measure impedance of one or more tissues based on an injected current, a portion of which passes through those tissues. By way of example, and not limitation, various implementations may advantageously provide improved sensitivity for detecting pulmonary edema and/or ventricular volume change.

In some embodiments, the implantable device 30 may include additional can, header, or superior vena cava electrodes to facilitate other measurement configurations. Some implantable devices that are configured to perform, for example, tripolar measurements may be changed in structure, operation, and algorithm to include two or more voltage sensing electrodes positioned within the superior vena cava 24. Examples of apparatuses and methods of using implanted electrodes to perform impedance measurement are described in U.S. Pat. No. 7,313,434, the contents of which are incorporated herein by reference.

Wires 44a, 44b, and 48 may be formed, for example, as traces on a printed circuit board, for example. The can electrode 46 may comprise a substantial portion of an external surface of housing 32, such that the interface impedance of the can electrode 46 is relatively low. The implantable device 30 may be, for example, a pacemaker or defibrillator (or a combination of both), or an infusion pump, and may be sized for implantation in a chest region of a patient. Although the implantable device 30 is shown in FIG. 2 to the left of the heart 12 and lungs 14, as in a right-sided implant location in a chest region of a patient, the device 30 may alternatively be implanted at a left-sided implant location in a chest region of a patient, such as in a left pectoral region.

The implementation shown in FIG. 2 may permit current to be injected between an electrode in or around the heart and an electrode on a device implanted in a chest region of a patient. The injected current may induce a voltage potential that can be measured across electrodes positioned in a vena cava of the patient. The injection and measurement can be repeated and measurements can be compared or compared to threshold values to assess physiologic changes in the patient such as lung edema development or heart enlargement, or both.

Transfer impedances can be calculated as ratios of the measured voltage potentials divided by the injected currents. Changes in transfer impedances can be monitored. The implementations discussed herein may provide improved sensitivity to these and other physiologic changes, which may permit better and earlier detection of the condition or conditions such that timely interventions may be initiated or modified, if appropriate.

Figure 3:
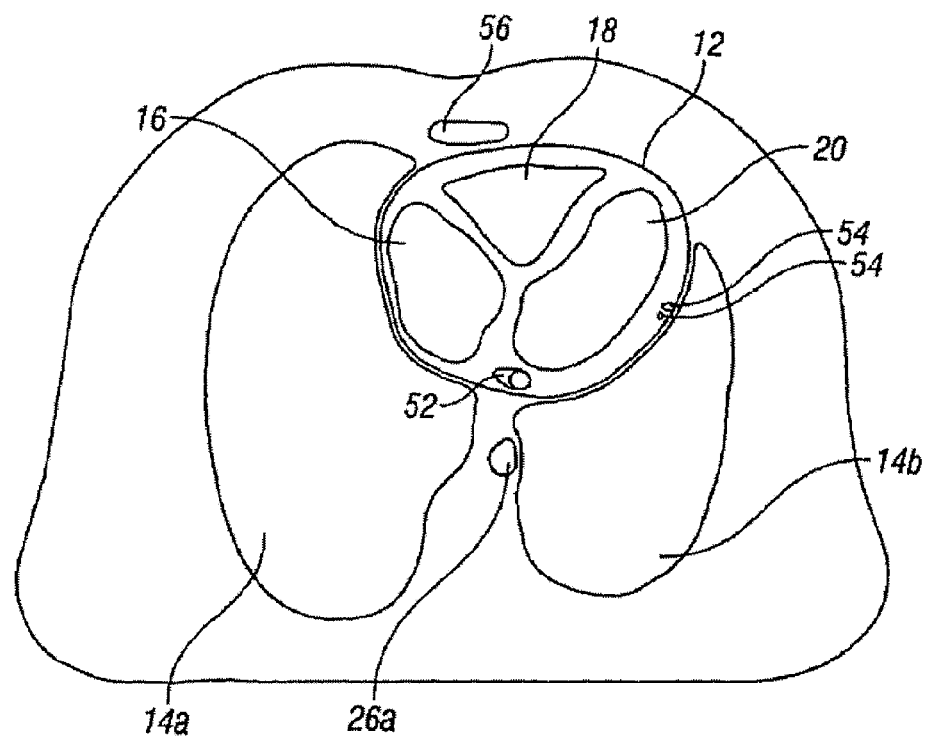
FIGS. 3-4 are cross-sectional views of a human thorax through the heart and lungs, the cross-sections being indicated in FIG. 1.

FIG. 3 shows an anatomical cross-section of FIG. 1 to illustrate a human thorax, including the heart 12 and lungs 14 through a transverse plane that shows the proximity of the left ventricle 20 to the left lung 14b. Specifically, FIG. 3 shows coronary veins 54 that can be the location, in some embodiments, for a left ventricular cardiac lead after passing through the coronary sinus 52. Similarly, the right atrium 16 has a proximal location to the right lung 14a, while the right ventricle 18 is not as close to either lung 14a, 14b. A descending portion 26a of the aorta 26 (referred to as the descending aorta), and a sternum 56 are also shown.

Figure 4:
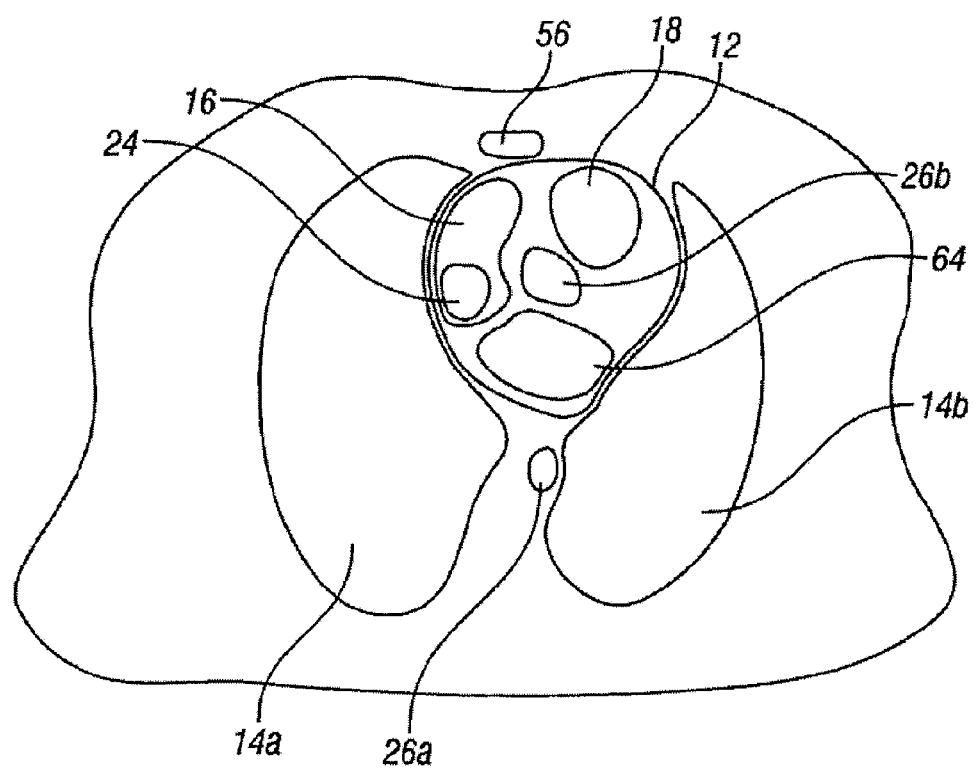

FIG. 4 shows another anatomical cross-section of a human thorax through a superior or higher transverse plane than that shown in FIG. 3. In FIG. 4, the superior vena cava 24 is shown entering the right atrium 16. Similar to the view of FIG. 3, FIG. 4 shows that the superior portion of right ventricle 18 is not close to the lungs 14. FIG. 4 shows both the descending aorta 26a, and also an ascending portion 26b (referred to as the ascending aorta) of the aorta 26. The left atrium 64 is shown, along with the sternum 56.

Figure 5:
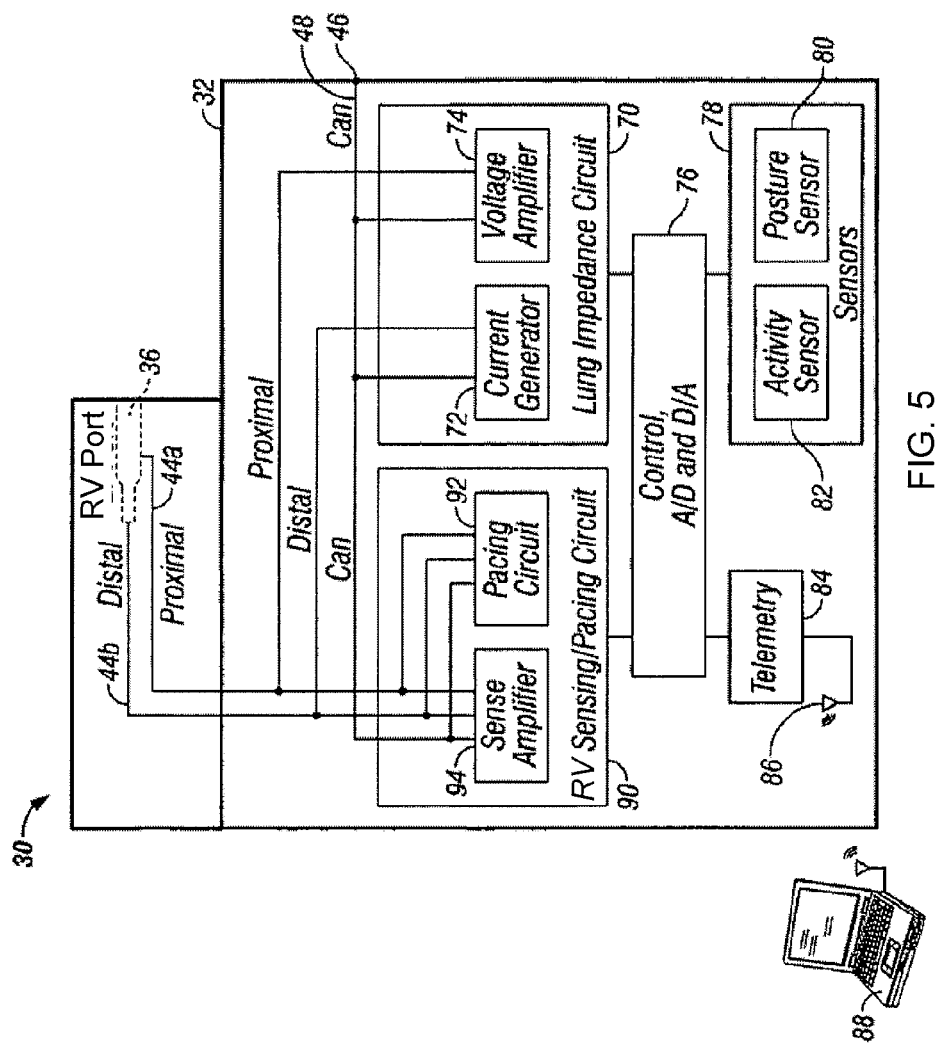
FIG. 5 is a more detailed view of an embodiment of the device shown in FIG. 2, showing a block diagram of circuitry within the device and an external device.

FIG. 5 shows a block diagram circuit representation of the implantable device 30 from FIG. 2. Device 30 includes circuits for measuring impedance and making pulmonary edema assessments, and communication circuits for interfacing with external devices. A lung impedance circuit 70 includes a current generator 72, which may inject an electrical current between two electrodes, such as the tip electrode 205, which may be positioned within the right ventricle 18 (FIG. 2) and the can electrode 46 over wire 48 and a conductor through lead 38 (not shown in FIG. 5). Thus, by virtue of positions of the electrodes, part of the current may flow across the right lung 14a. FIG. 5 is a simplified representation of a device, and for simplicity is not intended to show all connections or components that may be included in an actual implanted device of the type discussed herein. For example, the device in FIG. 5 shows only two connections 44a, 44b to the port 36, but there may be three, four, five, or more such connections for establishing electrical connections to three, four, five, etc. electrodes on a lead to be attached to the port 36. For example, the implementation depicted in FIG. 2 may include three wires 44 because the lead 38 includes a tip electrode 205 and two vena cava electrodes 42. Similarly, the device 30 may include a switch (not shown) that permits any of the electrodes to be configured as a pace or stimulus electrode or a sense electrode with appropriate connection to the sense, pace, current generator, or voltage amplifier block, as desired.

The injection current may be an alternating current (AC) or a direct current (DC). For example, an AC current may be injected between the current injection electrodes, such as the tip electrode 205 and the can electrode 46. To avoid undesirable polarization and electrolytic degradation effects at the electrodes and if cardiac stimulation is not desired, the injected current may be of such magnitude, frequency, and duration that it does not cause cardiac stimulation or activation. In one implementation, the AC current may have a frequency of about 50 KHz-100 KHz. Examples of possible current waveforms include sine waves and biphasic pulses (symmetric or otherwise). In some implementations, a cardiac stimulation pacing pulse may be used as the injection current. Alternatively, a DC current can be injected between the current injection electrodes, such as the tip electrode 205 and the can electrode 46. The current may follow various paths through the chest between the electrodes 205 and 46. Some of the current passes through the lungs 14a, 14b. Varying levels of fluid buildup in the lungs 14a, 14b can cause the lungs 14a, 14b to present variable impedances to the currents passing through them. Some of the currents also flow through the superior vena cava, and the voltages induced by these currents can be detected by the superior vena cava electrodes 42a and 42b.

The injection current between the electrodes 205 and 46 (see FIG. 2) creates an electric field in the body of a patient. Thus, a voltage potential appears between electrodes 205 and 46. A voltage amplifier 74 may then measure the voltages sensed between any two electrodes of the system, such as between the electrodes 205 and 46, or between the electrodes 42a and 42b. The voltage amplifier may, for example, be a signal-conditioning unit to measure the voltage, and may optionally include a demodulator. In some embodiments, the signal-conditioning may include sampling with analog and/or digital (e.g., IIR, FIR) filtering.

A control block 76 receives or contains information on the magnitudes of both the injected current and the resulting measured voltage. Analog-to-digital (A/D) converters may be used to translate the information. A processing unit (not shown) such as a microprocessor, microcontroller, or digital signal processor within the control block 76 may then use the current and voltage information to calculate impedance by dividing voltage by current. As body tissue fluid levels increase, the tissue impedance decreases. Thus, the impedance ratio may be used to assess pulmonary edema, and a degree of pulmonary edema may be determined for the patient. An algorithm describing the edema value determination will be discussed later.

The control block 76, as is conventional, may additionally include read-only memory (ROM), random-access memory (RAM), flash memory, EEPROM memory, and the like, which may store instructions that may be executed by the processing unit, as well as digital-to analog (D/A) converters, timers, counters, filters, switches, etc. (not shown). Impedance measurements and edema values may also be stored in memory. These control block components may be integrated within a single device, such as an application specific integrated circuit (ASIC), or alternatively may be located in separate devices. Appropriate busses (not shown) allow communication between components within control block 76.

Information from a sensor block 78 may be used to adjust the relationship between the measured impedance and the degree of edema. A posture sensor 80 may provide patient orientation information to the control block 76, allowing posture compensation to be included in the assessment of edema. Because organs and excess fluid in the thorax and lungs 14 tends to shift with posture changes due to gravity, measured impedance may vary as a patient assumes different positions. For example, when some patients lie on a right side, fluid and tissues in the left lung 14b may gravitate towards the mediastinum near the superior vena cava electrodes 42, which may result in lower measured impedance. Thus, based on posture sensor information, the relationship between the impedance measurement and the degree of edema may be adjusted to compensate. Similarly, that relationship may be inversely adjusted for a patient lying on his/her left side. Several types of posture sensors could be used, including mercury switches, DC-accelerometers, or other piezoelectric devices.

An activity sensor 82, conventionally used to aid in pacing applications, may also provide information to the control block 76. By using these compensation schemes, edema interpretation errors caused by postural fluid shifts within a patient may be avoided. Either sensor 80, 82 may optionally be excluded from the implantable device 30.

A telemetry block 84 may communicate wirelessly using radio frequency (RF) transmissions over an antenna 86 with a similarly wirelessly equipped monitoring unit 88. Monitoring unit 88 may be a computer (custom programmer, desktop, laptop, handheld, etc.), a telemedicine home station, a wearable device such as a wristwatch, or any other appropriate device, and may be used to program the implantable device 30, or to retrieve information, such as impedance measurements and edema values. A right ventricular sensing/pacing circuit 90 includes a pacing circuit 92 and a sense amplifier 94 and is used to sense and/or stimulate (pace) right ventricular cardiac events. The generic lung edema impedance circuit 34 (FIG. 2) is not explicitly shown in FIG. 5, but may include several of the FIG. 5 blocks, or portions thereof. Conventional elements which may further be included in device 30 but are not shown include battery or power supply blocks, defibrillation circuits, and circuits for a left ventricular port.

Figure 6A:
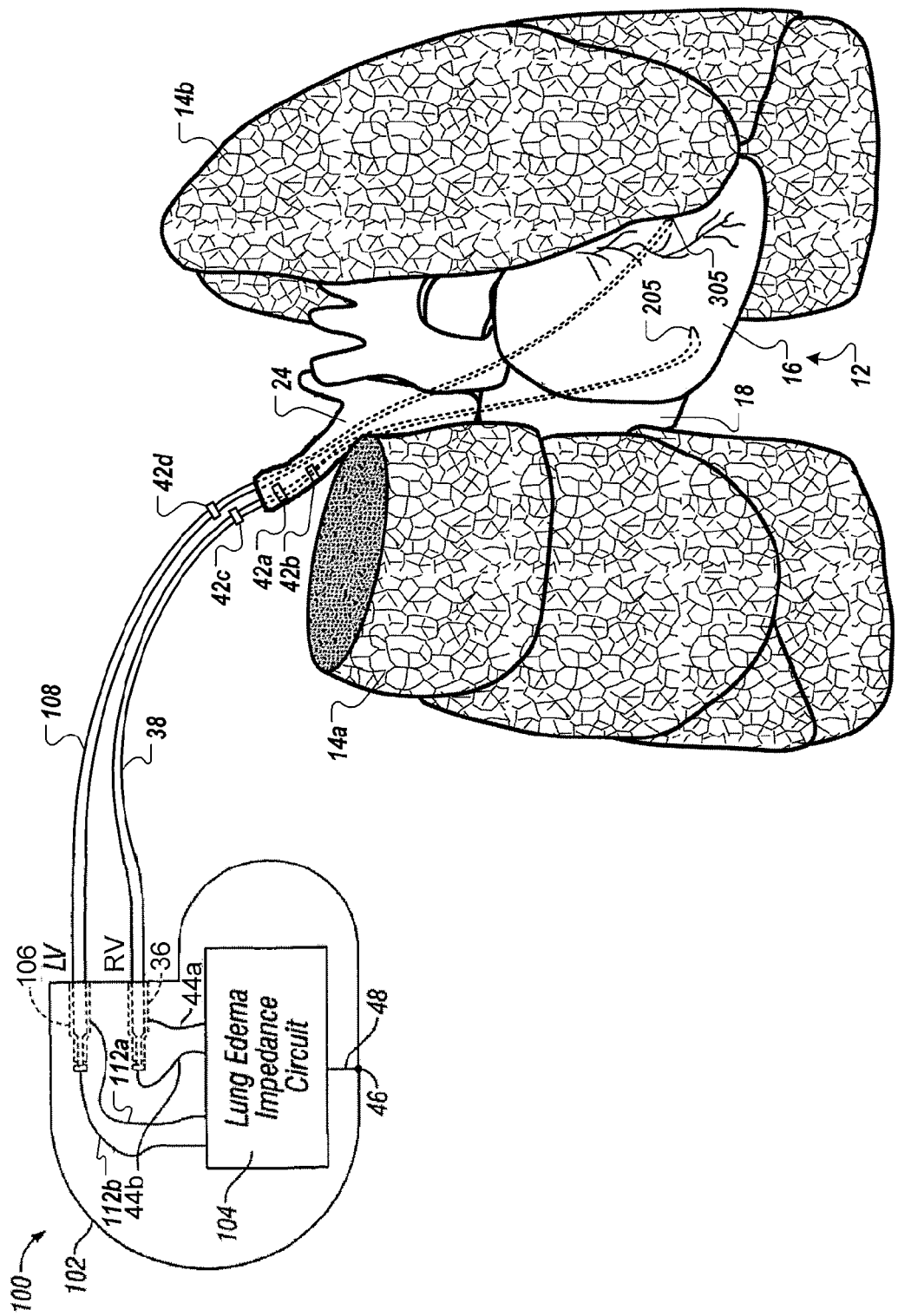
FIGS. 6A-6B are diagrams of an example implantable device.

FIG. 6A depicts an exemplary embodiment showing the heart and lungs from FIG. 1 and the implantable device 100. The implantable device 100 includes a housing 102 that houses a lung edema impedance circuit 104, and includes a right ventricular port 36 for attaching a right ventricular cardiac lead 38, and a left ventricular port 106 for attaching a left ventricular cardiac lead 108. The left ventricular lead 108 may be introduced into the venous system, down the superior vena cava 24, and on left ventricle 16, for example by way of the coronary sinus. For example, the left ventricular lead 108 can be located in coronary veins 54 (FIG. 3) of the left ventricle 16. In this example, the right ventricular lead 38 has proximal and distal electrodes 42a, 42b that are electrically connected to conductors (not shown) that run through the right ventricular lead 38. The conductors connect to conducting wires 44a, 44b, respectively, within the device 100 when the right ventricular lead 36 is attached to the right ventricular port 36, establishing electrical connections between the lung edema impedance circuit 104 and the right ventricular electrodes 42a, 42b. Similar to the right ventricular lead 38, the left ventricular lead 108 may have additional or fewer electrodes, and/or may alternatively use a tip electrode 305, for example.

In the depicted example, the right ventricular lead 38 further includes an electrode 42c. The left ventricular lead 108 also includes an electrode 42d. In some examples, one or both of the electrodes 42c, 42d may be positioned at predetermined locations within in the superior vena cava 24. In some implementations, the electrodes 42c, 42d, can be used to provide additional spacings for taking impedance measurements between the electrodes 42c, 42d, and the can electrode 46, the superior vena cava electrodes 42a, 42b, and/or the tip electrodes 205, 305. By using the electrodes 42a-42d, two or more impedance measurements can be made to determine impedance changes caused by, for example, heart enlargement and/or pulmonary edema. The electrodes 42c and 42d are respectively connected to conductors that run through the respective lead, and to wires (not shown in FIG. 6A for simplicity) that couple the lung edema impedance circuit 104 to the conductors.

The arrangement depicted in FIG. 6A may facilitate lung impedance measurements from the right ventricle 18, the left ventricle 16, and the superior vena cava 24. As such, a more global measurement of lung impedance and hence a more global pulmonary edema assessment may be obtained by using a weighted combination of the multiple impedance measurements. The weighted combination may advantageously retain a high degree of specificity since each lead is anatomically located near the lungs 14. Furthermore, the combination may allow for a subtraction of common signal contributions from the heart and great vessels thereof, thereby allowing an even more lung-specific measurement.

Figure 6B:
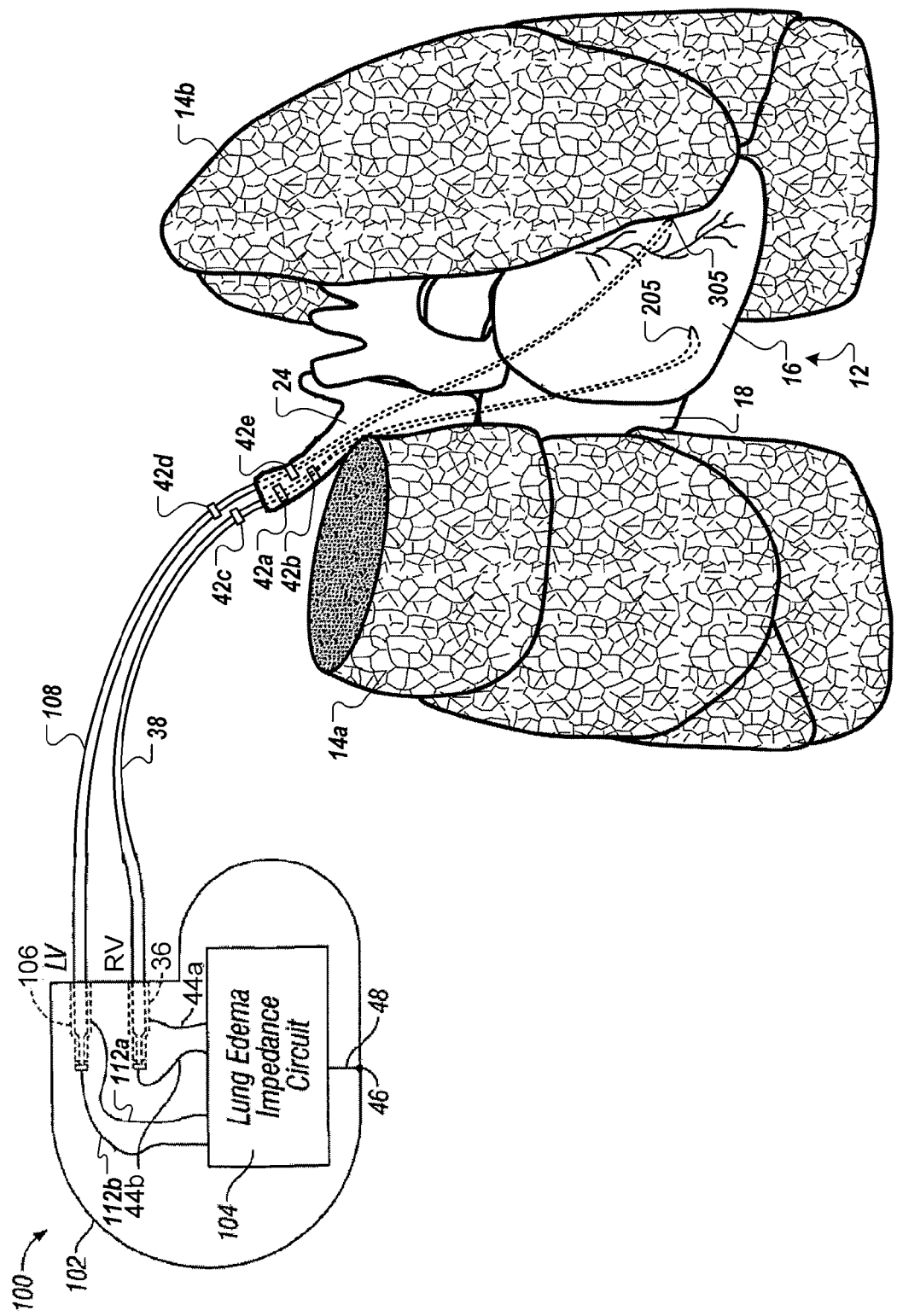

In another implementation, FIG. 6B depicts an exemplary embodiment showing the heart and lungs from FIG. 1 and the implantable device 100. The right ventricular lead 38 has proximal and distal electrodes 42a, 42b, 42c that are positioned at locations within the superior vena cava 24. The left ventricular lead 108 includes the electrode 42d and further includes an electrode 42e positioned within the superior vena cava and distally with respect to the electrode 42d.

In one example implementation configured for left ventricle-only pacing, transfer impedance measurements, such as described herein, may be made via the left ventricular lead 108 and the electrodes 42d, 42e positioned in the superior vena cava. Accordingly, some embodiments may assess pulmonary edema by making transfer impedance measurements that include electrodes positioned within the superior vena cava to sense voltage without the right ventricular lead 38, for example.

Figure 7:
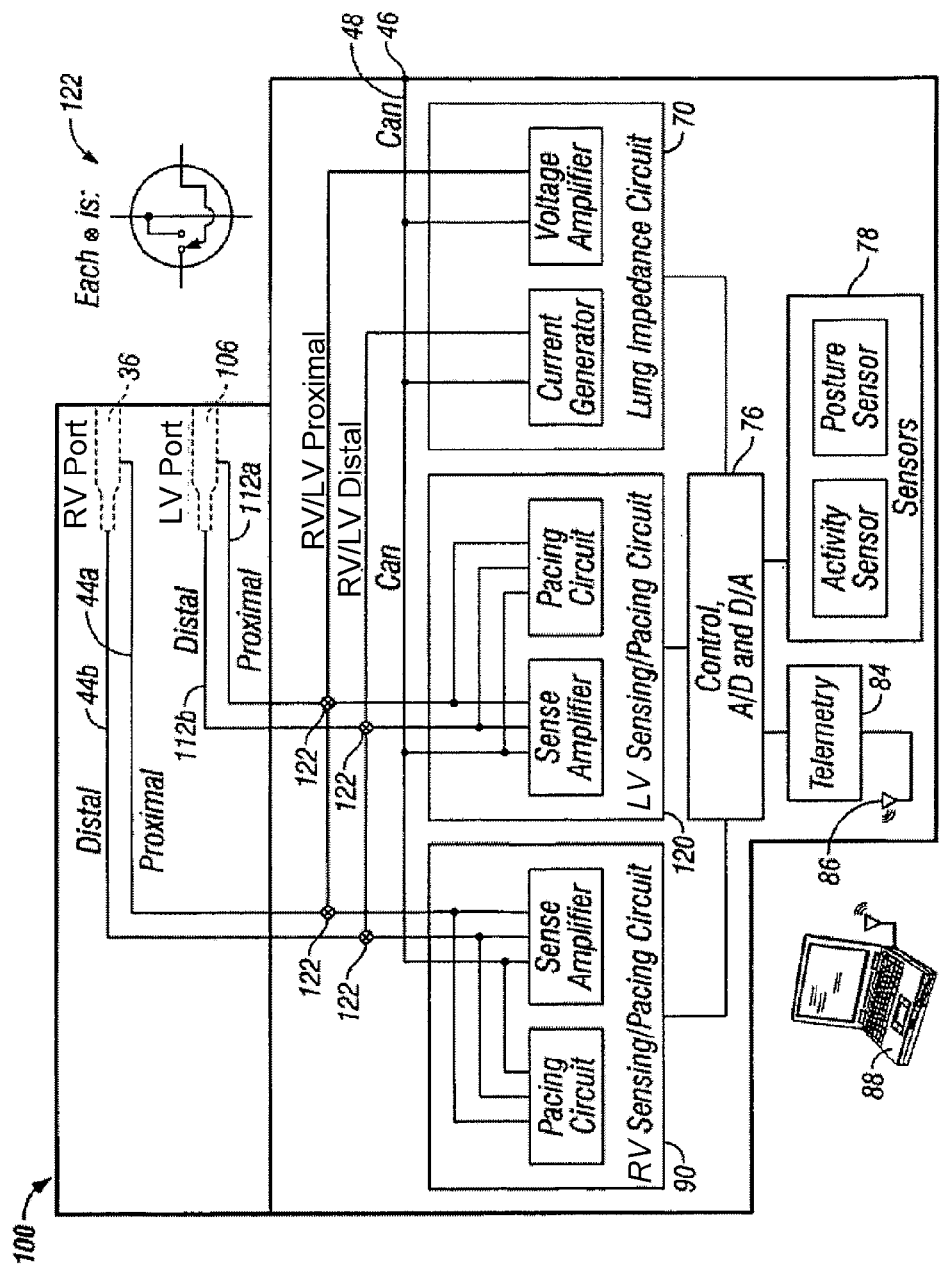
FIG. 7 is a more detailed view of an embodiment of the device shown in FIG. 6, showing a block diagram of circuitry within the device, an external device, and a switch.

FIG. 7 shows a block diagram circuit representation of the example implantable device 100 from FIG. 6. FIG. 7 is similar to FIG. 5, with the addition of a left ventricle sensing/pacing circuit 120 for sensing and/or stimulating left ventricle cardiac events, and the addition of the left ventricle port 106. An implementation may use a single lung impedance circuit 70 and switch connections in succession using switches 122 to obtain the right ventricular and left ventricular impedance measurements. An exploded view of switch 122 is shown in the upper right corner of FIG. 7. Switches 122 may be controlled by control unit 76 (details not shown in FIG. 7). As with FIG. 5, FIG. 7 is a simplified representation not intended to show all connections or components that may be included in an actual implanted device of the type discussed herein. For example, while only two wires are shown connecting to each port for simplicity, an appropriate number of wires may be included so that electrical connections may be established between lead electrodes and device circuits.

Figure 8A:
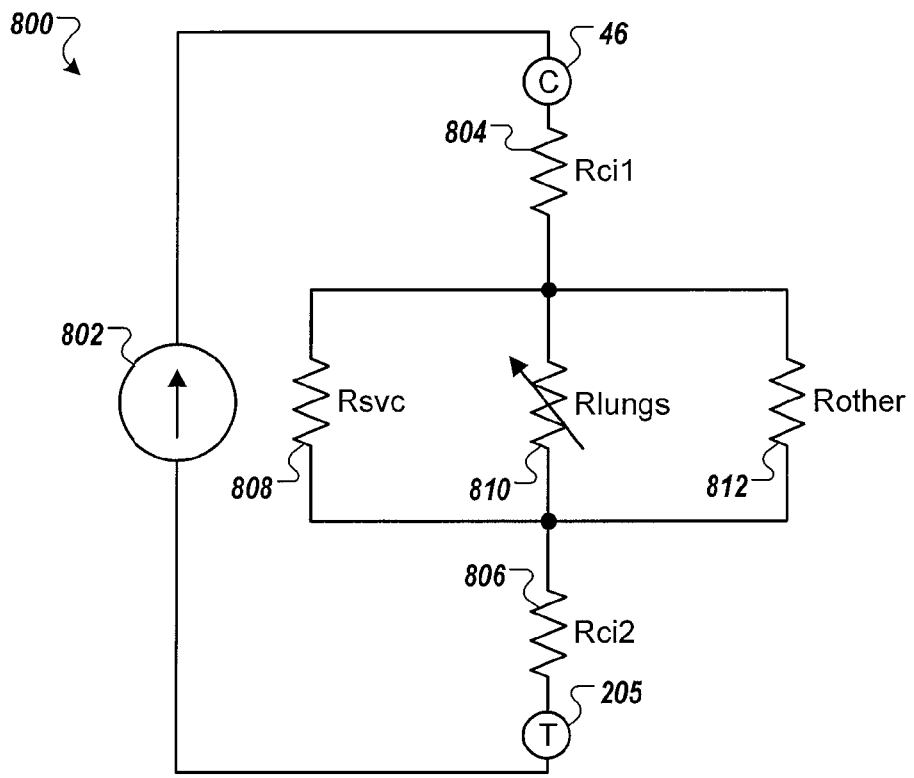
FIGS. 8A-8B are conceptual models of current paths through a human thorax between the electrodes of exemplary implantable devices.
Figure 8B:
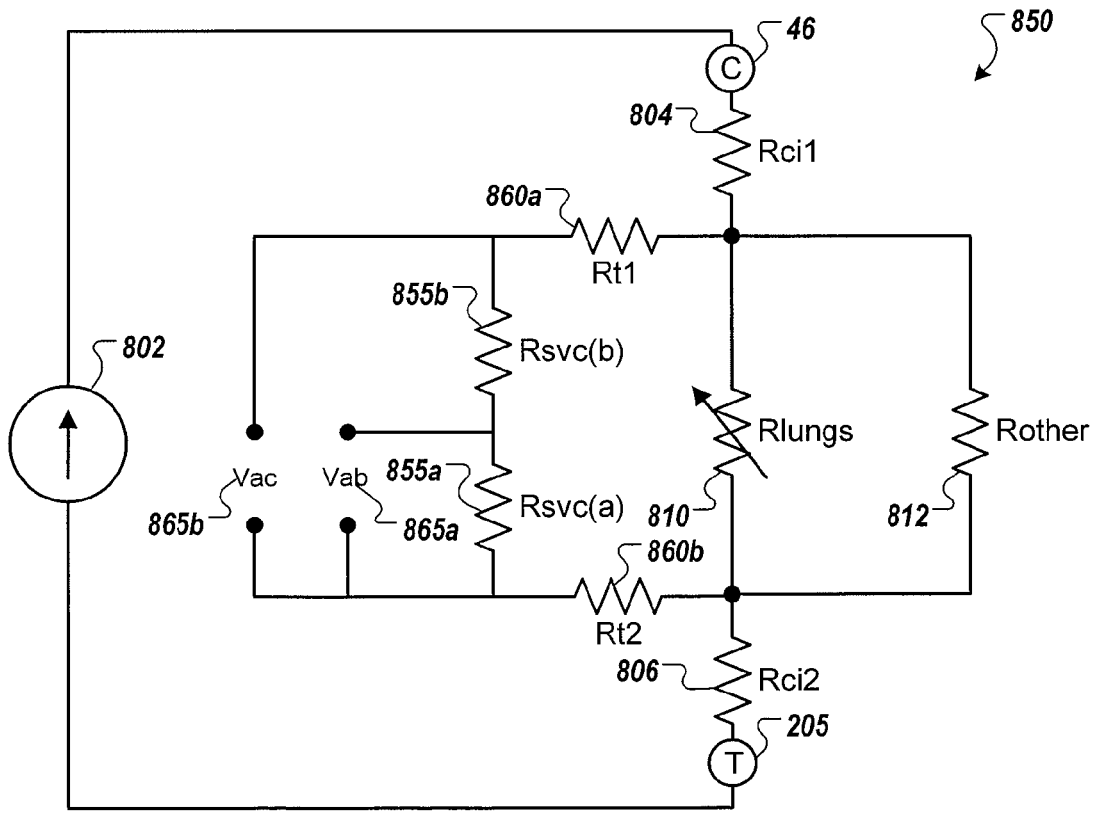

FIGS. 8A-8B are exemplary conceptual models of current paths through a human thorax between the electrodes of the example implantable devices of FIG. 2 and FIG. 6. The models are simplified circuit representations of current paths through the human thorax. FIG. 8A shows a conceptual model 800 of an electrical system in one embodiment. The model 800 includes a current source 802 (e.g., the lung edema impedance circuit 34) that may inject current between the tip electrode 205 and the can electrode 46. The can electrode 46 has an associated connector interface impedance (Rci1) 804, and the tip electrode 205 has an associated connector interface impedance (Rci2) 806. In some implementations, the connector interface impedances 804, 806 can include impedances associated with tissues that form in response to the implantation of the implantable device 30 and/or the tip electrode 205.

The model 800 further includes impedance elements representing impedances in the superior vena cava 24, the lungs 14a, 14b, and other tissues that have impedances associated with them. In the depicted example, a current injected by the current source 802 is divided among a superior vena cava impedance (Rsvc) 808, a lung impedance (Rlungs) 810, and other tissue impedance (Rother) 812.

In some implementations, the superior vena cava impedance (Rsvc) 808 may remain substantially constant, while the lung impedance (Rlungs) 810 may fall substantially as a function of increasing pulmonary edema, for example. Accordingly, voltage measured between electrodes in the superior vena cava may fall in response to injected current shifting away from the Rsvc 808 impedance path as the impedance of the Rlungs 810 path falls in response to increased fluid in the lungs.

In various embodiments, the location of the voltage sensing electrodes in the superior vena cava may further advantageously reduce the sensitivity of current distribution through Rsvc 808, Rlungs, 810, and Rother 812, and thus the impedance measurement, to changes in heart volume.

In some implementations, accumulations of fluid in the lungs 14a, 14b due to pulmonary edema can cause the lung impedance 810 to vary. Two or more electrodes positioned within the superior vena cava 24 can be used to measure an impedance by sensing one or more voltages induced by a current injected via an electrode located in or around the heart. For example, lungs that are substantially free from fluid buildup can have a relatively high value for the lung impedance 810, whereas lungs with a fluid buildup can have a relatively lower lung impedance 810. Therefore, in a patient with fluid present in the lungs, the reduced lung impedance 810 may cause the current injected between the tip electrode 205 and the can electrode 46 to proportionally shift away from the superior vena cava 24 (Rsvc) path in favor of a path through the lungs (Rlungs). In some implementations, superior vena cava impedance 808 measurements can vary with the amount of fluid present in the lungs, and these measurements can be used to detect the presence and/or degree of pulmonary edema.

FIG. 8B shows a simplified conceptual model 850 of the implantable device 100. The model 850 also includes a first tissue impedance 860a that represents the impedance caused by the tissues that form the current path between the superior vena cava electrodes 42a-42d and the first connector interface impedance 804. A second tissue impedance 860b represents the impedance of tissues that contribute to a second current distribution between the superior vena cava electrodes 42a-42d and the second connector interface impedance 804. Examples of tissues that contribute the first tissue impedance 860a may include, by way of example and not limitation, the walls of the superior vena cava 24, the upper portions of the lungs 14a, 14b, muscles, and/or other tissues that provide an electrical pathway for current. Examples of tissues that can contribute to the tissue impedance measurements may include, by way of example and not limitation, the walls of the superior vena cava 24, blood, the walls of the heart, lower portions of the lungs 14a, 14b, muscle tissues, connective tissues (e.g., fascia), fat, and/or other tissues that provide an electrical pathway for current.

The model 850 includes a first superior vena cava impedance 855a and a second superior vena cava impedance 855b. The first superior vena cava impedance 855a represents the impedance calculated from a first voltage difference 865a measured between the superior vena cava electrodes 42a and 42b. The second superior vena cava impedance 855b represents the impedance calculated from a second voltage difference 865b measured between the superior vena cava electrodes 42a and 42c, or between electrodes 42a and 42d.

The first voltage difference 865a represents the voltage difference associated with the spacing between the superior vena cava electrodes 42a and 42b, and the second voltage 865b represents the voltage difference associated with the spacing between the superior vena cava electrodes 42a and 42c. In some other examples, two, three, or more voltages can be measured between various other combinations of differently spaced electrodes located in or near the superior vena cava 24 to determine the contributions of impedance changes due to heart enlargement and/or pulmonary edema.

A number of simulations were conducted using a computer modeling technique. In some examples, simulation results indicate that increased lung impedance measurement sensitivity is possible in various embodiments. A three-dimensional computer model that divides a model of a human thorax into several million small volumes, each corresponding to body tissue, was used to simulate lung impedance under normal and pulmonary edema conditions. Each small tissue volume was assigned an appropriate electrical resistivity (e.g. blood=150 ohms-cm, normal lung=1400 ohms-cm, skeletal muscle=225 ohms-cm, heart muscle=250 ohms-cm, etc.) according to published tables. Electrodes were then placed at various locations in the model, and current may be injected. The simulation program was run on the computer to calculate the resulting voltage potentials at each of the volumes using electric field equations. The results can be used to compute impedance by dividing the measured potentials by the injected current.

Figure 9:
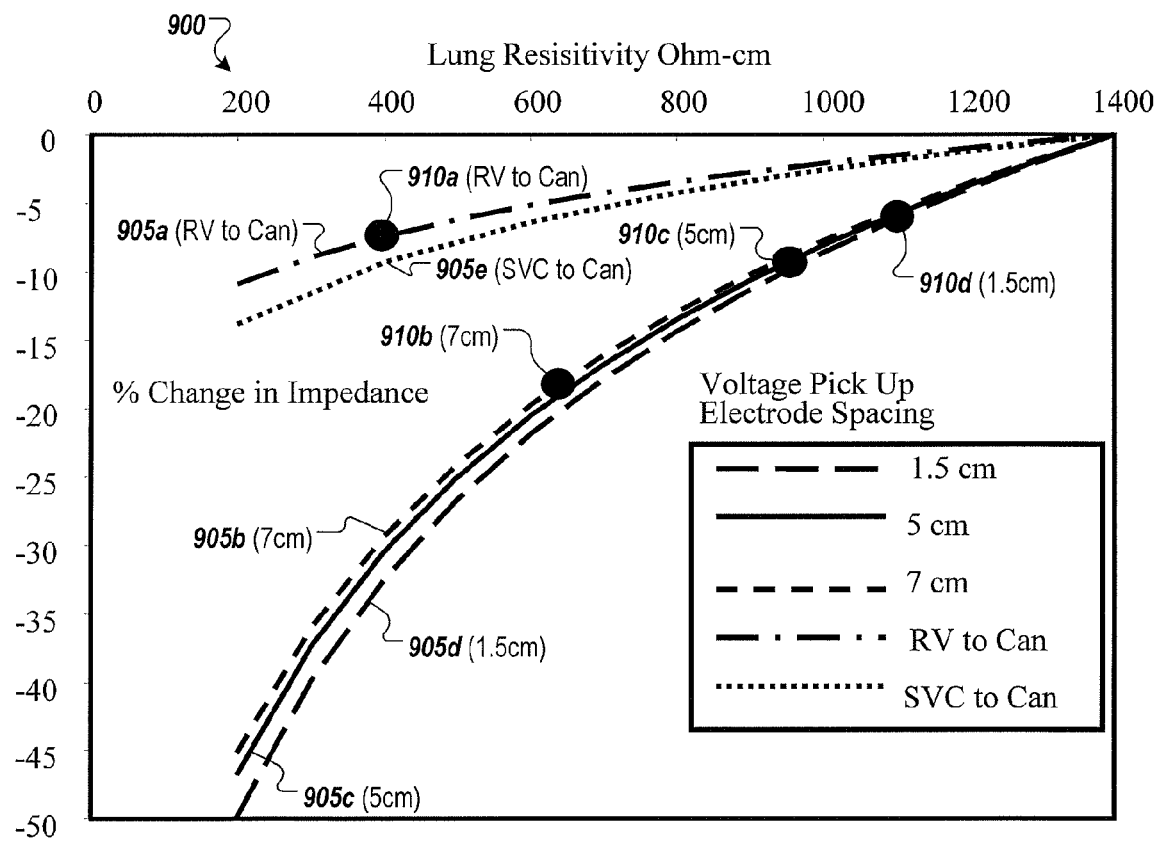
FIG. 9 is a chart that shows example impedance values at several electrode spacings and lung resistivities.

FIG. 9 is a chart 900 that shows example impedance values at several electrode spacings and lung resistivities. In general, simulated tests have shown substantially improved measurement sensitivity for determining a transfer impedance by injecting a current between one pair of implanted electrodes (e.g., the tip electrode 205, can electrode 46) and measuring voltage associated with the injected current between another pair of electrodes (e.g., two of the electrodes 42a-42c) positioned in the superior vena cava. In various examples, such transfer impedance measurements (using voltage measurements between two sense electrodes that differ from two current injection electrodes used to inject a current that induces the measured voltage, where the transfer impedance is a ratio of such a measured voltage divided by such an injected current) may provide enhanced sensitivity to detect and/or quantify pulmonary edema, and may further advantageously be extended to quantitatively assess how much other tissues (e.g., heart volume) contribute to measured impedance values.

The chart 900 shows five example curves. The chart 900 includes a tip to can curve 905a that represents the percent change in impedance sensed between the tip electrode 205 and the can electrode 46 within a range of lung resistivity values. The chart 900 includes a 7 cm curve 905b that represents the percent change in impedance sensed by a pair of superior vena cava electrodes (e.g., a pair of the electrodes 42a-42d) spaced 7 cm apart. The chart 900 also includes a 5 cm curve 905c that represents the percent change in impedance sensed by a pair of superior vena cava electrodes spaced 5 cm apart, and a 1.5 cm curve 905d that represents the percent change in impedance sensed by a pair of superior vena cava electrodes spaced 1.5 cm apart. A SVC to can curve 905e represents the percent change in impedance sensed between the can electrode 46 and a single one of the superior vena cava electrodes 42a-42d.

The curves 905a-905e represent the results of the previously described simulated tests for measuring the impedances caused by pulmonary edema and heart enlargement. In the simulation, pulmonary edema was simulated by reducing the electrical resistivity of the simulated lung tissue.

When compared to the tip to can curve 905a or the SVC to can curve 905e, which involve only a single electrode in the superior vena cava, the curves 905b-905d show improved sensitivity by increased percent changes in sensed lung impedance. For example, in a lung with pulmonary edema that exhibits a 1000 Ohm-cm resistivity, the tip to can curve 905a and the SVC to can curve 905e show an approximately −1% change in sensed impedance, whereas the curves 905b-905d show that the 7 cm, 5 cm, and 1.5 cm spaced electrodes exhibit an approximately −7% to −8% change in sensed impedance.

In lungs that are experiencing pulmonary edema, the buildup of fluid can lower lung resistivity, and the use of spaced electrodes in the superior vena cava 24 can be used to sense the degree of edema with greater sensitivity than can be done by measuring the impedance between the tip 46 and can 205 electrodes alone. For example, in a lung that exhibits a 400 Ohm-cm resistivity, the tip to can curve 905a shows an approximately −8% change in sensed impedance and the SVC to can curve 905e shows an approximately −10% change, whereas the 7 cm curve 905b shows an approximately −28% change. Likewise, the 5 cm curve shows an approximately −30% change, and the 1.5 cm curve shows an approximately −32% change. These simulated results indicate that an approximately 300% improvement in sensitivity to pulmonary edema can be obtained at a lung resistivity of 400 Ohm-cm by using impedance measurements taken from pairs of electrodes spaced in the superior vena cava 24. Improvements of approximately 600%-800% were determined at a lung resistivity of 1000 Ohm-cm.

The chart 900 also includes four markers that indicate how much the sensed impedances would change if only the heart enlarged, which is common in heart failure patients. In other words, how measured impedances may be affected by heart enlargement but without pulmonary edema. In the example simulation results, a marker 910a represents the impedance change caused by a 30% enlarged heart and sensed between the tip electrode 205 and the can electrode 46. A marker 910b shows the effect of the 30% enlarged heart at superior vena cava electrodes spaced 7 cm apart, a marker 910c shows the effect of the 30% enlarged heart at superior vena cava electrodes spaced 5 cm apart, and a marker 910d shows the effect of the 30% enlarged heart at superior vena cava electrodes spaced 1.5 cm apart. The marker 910a shows that the 30% enlarged heart will cause an approximately −8% change in sensed impedance, whereas the 7 cm curve shows an approximately −17% change. The 5 cm and 1.5 cm curves 905c, 905d, show that the 30% enlarged heart results in changes of approximately −10% and −5%, respectively. As can be seen in FIG. 9, the −8% impedance change due to heart enlargement for configuration 905a is about the same change as would be seen for a lung resistivity of 400 Ohm-cm for a given severity of pulmonary edema. Similarly, the impedance changes of −17%, −10%, and −5% for configurations 905b, 905c, and 905d, respectively, correspond to impedance changes seen at in edematous patients having lung resistivities of 625 Ohm-cm, 950 Ohm-cm, and 1125 Ohm-cm.

Implementations discussed herein can be used to inject currents, measure voltages, and calculate impedance values that can be used to solve equations to determine, for example, contributions to impedance changes due to pulmonary edema or heart enlargement.

Figure 10:
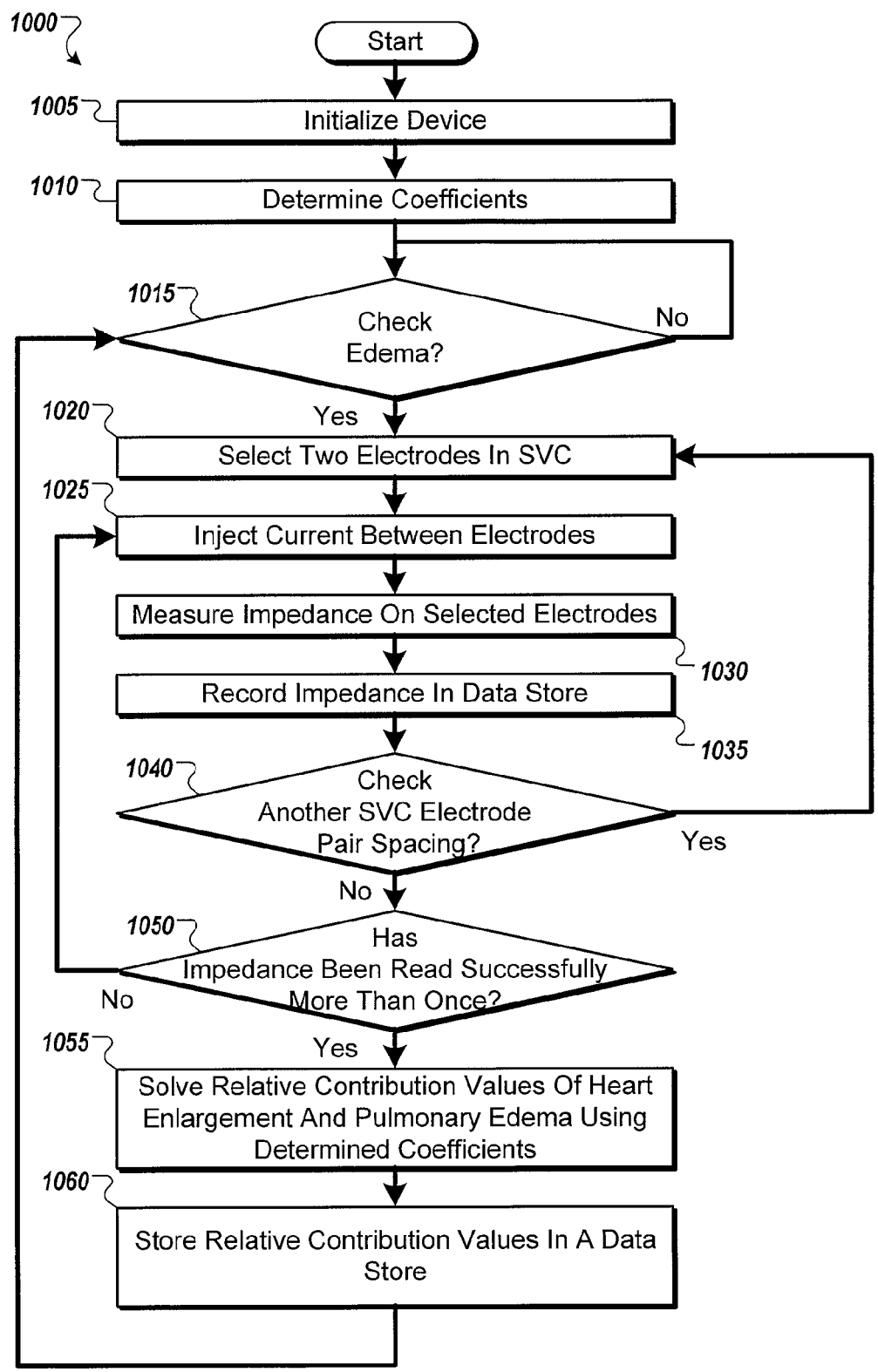
FIG. 10 is a flowchart of an example process for measuring biological impedance values for the detection of pulmonary edema.

FIG. 10 is a flowchart of an example process 1000 for measuring biological impedance values for the detection of pulmonary edema using two or more voltage sensing electrodes positioned in the superior vena cava. The process 1000 begins when a device (e.g., the device 30 of FIG. 2, or the device 100 of FIG. 6) is initialized 1005. In some examples, initialization may include determining coefficients for a system of equations, as discussed elsewhere herein. Various approaches may be used to determine the coefficients (e.g., A, B). For example, a simulation model may be used to separately change the lungs resistivity and heart volume in order to measure the impedance value response(s). This may be particularly effective for a patient who has similar anatomical characteristics to the one used in the model. In some other implementations, initialization may involve measurements associated with body characteristics. For example, predetermined body position changes may be made to manipulate fluid levels and/or distribution. In some examples, a predetermined routine of body positioning may involve a Valsalva Maneuver, which is a respiratory maneuver that can impact heart volume. After initialization 1005, a number of coefficients are determined 1010. For example, an impedance measurement (e.g., Z(ab)) can be recorded and stored in a data store for subsequent processing. For example, such subsequent processing may use a formula of the form Z(ab)=A(Z(lung))+B(Z(heart)), where the coefficients A and B can be experimentally determined constants. In some implementations, the coefficients can be determined 1010 from a look-up table or other collection of coefficient values. In some examples, a look-up table may be determined from a model using data for patients of a number of gender, height, and/or weight profiles. In some implementations, the coefficient values can be determined through a self-calibration routine.

For each electrode spacing measurement that is checked, a corresponding additional equation and an additional unknown may be included in the system of equations to be solved. Each unknown may be defined to correspond to an impedance of an additional tissue. For example, with three electrode spacings for electrodes positioned in the superior vena cava, the measurements may be solved for the relative contributions to impedance and/or impedance values of muscle, lungs, and heart tissues.

Some further embodiments may include more than two electrodes for injecting current. For example, a system may inject current between an additional electrode positioned in a location adjacent a lung but substantially separate from the can (housing) of the implanted device, thereby providing a substantially altered current distribution for the injected current. Similarly, various combinations of injection electrodes may include one or more injection electrodes positioned in or around the heart, for example. In such embodiments, measurements include potentials sensed at two or more electrodes positioned within the superior vena cava.

In some implementations, the device can perform an edema check at timed intervals and/or in response to events. For example, the device can be configured to perform an edema check every second, minute, 5 minutes, 15 minutes, hour, day, or other interval. In another example, the device can be configured to perform (or delay performance of) an edema check in response to events sensed by the activity sensor 82 and/or posture sensor 80, and/or in response to a command received by the telemetry block 84 from the monitoring unit 88.

If an edema check is not determined 1015 to be needed, then the process 1000 loops back to continue to await a trigger for an edema check. If an edema check is determined 1015 to be needed, then two electrodes in the superior vena cava are selected 1020. A current is injected 1025 between the two electrodes, and an impedance is measured 1030 on the selected electrodes. In some implementations, a current is injected between two electrodes different from the SVC electrodes, such as between an electrode in or around the heart and a can electrode on the implantable device, a voltage is measured between the two SVC electrodes, and a transfer impedance is calculated as a ratio of the measured voltage divided by the injected current. The impedance is recorded 1035 in a data store, such as a non-volatile memory of the device.

If another superior vena cava electrode spacing impedance check is determined 1040 to be needed, then steps 1020-1035 are repeated.

If another superior vena cava electrode spacing impedance check is not determined 1040 to be needed, then in some implementations, it may be desirable to use multiple impedance checks to measure edema, for example using the same pair of SVC electrodes. For example, bodily motion, aging leads, movement or shifting of the electrodes may briefly interfere with an impedance check, and by using multiple readings any erroneous readings may be detected and ignored.

If the impedance has not been read successfully 1050 more than once, then another edema check is performed by injecting 1025 current between the electrodes. If the impedance has been read successfully 1050 more than once, then the relative contributions of heart enlargement and pulmonary edema are solved 1055 using the determined coefficients. For example, the formulas Z(ab)=A(Z(lung))+B(Z(heart)) and Z(bc)=C(Z(lung))+D(Z(heart)) can be used. Z(ab) represents the impedance measured between a first and second superior vena cava electrodes, and Z(bc) represents the impedance measured between the second and a third superior vena cava electrodes. By way of example and not limitation, the values A, B, C, and D may be experimentally determined coefficients, or determined from modeling of a particular patient. In some examples, these two equations with two unknowns may be solved for Z(lung)+Z(heart), the contribution of the lungs 14a, 14b and heart to the impedance change.

The relative contribution values are stored 1060 in the data store. In some implementations, the values can be later retrieved through the telemetry block 84 by the monitoring unit 88.

Although various embodiments have been described with reference to the figures, other examples are possible. For example, the system may capture voltages from each of the two, three, or more superior vena cava electrodes 42a-42d at substantially the same time while a current is being injected, and mathematically determine potentials between electrodes of interest.

In some examples, one or more of the electrode spacings may be referenced to a reference feature or location within the superior vena cava. For example, a reference feature within the superior vena cava 24 may include referring fluoroscopic positioning based upon external reference markers located on the patient's skin, bone structures, or other convenient reference features visible by way of fluoroscopic methods. In some examples, one or more additional leads may provide independent positioning of the superior vena cava electrodes 42a-42d relative to one or more predetermined reference features in the superior vena cava 24. Subsequent monitoring of the position of the superior vena cava electrodes 42a-42d relative to a desired position with respect to the reference feature may be used to modify or assess the quantitative measurements of pulmonary edema and/or heart enlargements, for example. As the position of at least one of the superior vena cava electrodes 42a-42d deviates from a desired position with respect to the reference feature, confidence in the measured pulmonary edema may decrease, for example.

Various embodiments may be implemented in systems, apparatus, or methods. In one exemplary aspect, a method for assessing pulmonary edema using an implantable medical device includes a step of injecting an electrical current between a first current electrode and a second current electrode, wherein the first current electrode is located in or around the heart. The method further includes a step of sensing a first voltage induced by the current at a first sense electrode located within the superior vena cava. The method further includes a step of sensing a second voltage induced by the current at a second sense electrode located within the superior vena cava and spaced apart from the first sense electrode. Finally, the method includes a step of determining an impedance value associated with lung tissue based upon the difference between the first and the second sensed voltages.

In various examples, the exemplary methods may involve assessing pulmonary edema based upon changes in the first impedance. The first current electrode may be positioned within the right ventricle. The second current electrode may be an implanted electrode spaced apart from the first current electrode. The methods may further using a third sense electrode located within the superior vena cava and spaced apart from the first sense electrode and the second sense electrode to sense a third voltage induced by the current. The second voltage difference between the first sense electrode or the second sense electrode and the third sense electrode may be measured to determine a second impedance. The changes in the second impedance may used to assess heart enlargement. The first sense electrode, the second sense electrode, and the first current electrode may commonly reside on a first lead. The first sense electrode, the second sense electrode, the third sense electrode, and the first current electrode may commonly reside on a first lead.

A number of implementations have been described. Nevertheless, it will be understood that various modifications may be made without departing from the spirit and scope. For example, advantageous results may be achieved if the steps of the disclosed techniques were performed in a different sequence, if components in the disclosed systems were combined in a different manner, or if the components were replaced or supplemented by other components. The functions and processes (including algorithms) may be performed in hardware, software, or a combination thereof, and some implementations may be performed on modules or hardware not identical to those described. Accordingly, other implementations are contemplated.

What is claimed is:

1. A method of monitoring pulmonary edema in a human being, the method comprising:
   injecting an electrical current between a first electrode located in or around a heart and a housing of a medical device implanted in a chest region;
   measuring a voltage potential between a second electrode in a superior vena cava and a third electrode in the superior vena cava, the voltage potential created by the electrical current;
   measuring a second voltage potential between a fourth electrode in the superior vena cava and either the second electrode or the third electrode; and
   assessing pulmonary edema based on (A) a first impedance value calculated from the electrical current and the voltage potential and a stored edema threshold impedance value and (B) a second impedance value calculated based on the electrical current and the second voltage potential.

2. The method of claim 1, wherein the injected electrical current is a cardiac pacing pulse configured to initiate a cardiac cycle.

3. The method of claim 1, wherein the injected electrical current is configured such that a cardiac cycle is not initiated in response to injection of the electrical current.

4. The method of claim 1, wherein the second electrode and the third electrode are positioned on a lead, a distal end of which is located in a right ventricle.

5. The method of claim 1, further comprising assessing heart enlargement based on the calculated impedance values.

6. The method of claim 5, wherein relative contributions to impedance changes attributable to pulmonary edema and heart enlargement are determined by solving a system equations using the calculated impedance values and predetermined coefficients.

7. The method of claim 1, wherein two of the second electrode, third electrode and fourth electrode are positioned on a first lead and the remaining electrode is positioned on a second lead.

8. The method of claim 1, wherein each of the second, third and fourth electrodes is positioned on a single lead.

9. The method of claim 1, wherein the current injection, voltage measurement, first impedance value calculation, and second impedance value calculation is repeated on a periodic basis and the assessing pulmonary edema includes assessing a change in edema based on two or more of the calculated impedance values.

10. A method of monitoring pulmonary edema in a human being, the method comprising:
    injecting an electrical current between a first electrode located in a fight ventricle of a heart and a housing of a medical device implanted in a chest region;
    measuring a voltage potential between a second electrode in a superior vena cava and a third electrode in the superior vena cava, the voltage potential created by the electrical current;
    measuring a second voltage potential between a fourth electrode in the superior vena cava and either the second electrode or the third electrode; and
    assessing pulmonary edema based on (A) a first impedance value calculated from the electrical current and the voltage potential and a stored edema threshold impedance value and (B) a second impedance value calculated based on the electrical current and the second voltage potential.

11. A method of monitoring pulmonary edema in a human being, the method comprising:
    injecting an electrical current between a first electrode located in a coronary vein of a left ventricle of a heart and a housing of a medical device implanted in a chest region;
    measuring a voltage potential between a second electrode in a superior vena cava and a third electrode in the superior vena cava, the voltage potential created by the electrical current;
    measuring a second voltage potential between a fourth electrode in the superior vena cava and either the second electrode or the third electrode; and
    assessing pulmonary edema based on (A) a first impedance value calculated from the electrical current and the voltage potential and a stored edema threshold impedance value and (B) a second impedance value calculated based on the electrical current and the second voltage potential.

12. An implantable medical device, comprising: a housing for the implantable device sized for implantation in a chest region of a patient and comprising a housing electrode; a lead port into which a proximal end of a lead is connectable, the lead having first, second, third, and fourth conductors that are insulated from one another and that extend from the proximal end of the lead to corresponding first, second, third, and fourth electrodes, the third electrode positioned near a distal end of the lead for location in or around a heart, the first, second, and fourth electrodes positioned on the lead for location in a superior vena cava;

an electrical impedance measurement circuit electrically connected to the lead port and the housing electrode, the circuit comprising a current generator, a voltage amplifier and a control module, the current generator designed to inject an electrical current between the third electrode located in or around the heart and the housing electrode, the voltage amplifier designed to measure a first voltage potential between the first and second electrodes located in the superior vena cava and a second voltage potential between a fourth electrode in the superior vena cava and either the second electrode or the third electrode, wherein the voltage potential is created by the electrical current, and the control module designed to assess pulmonary edema based on (A) a first impedance value calculated from the electrical current and the voltage potential and a stored edema threshold impedance value and (B) a second impedance value calculated based on the electrical current and the second voltage potential.

13. The device of claim 12, wherein the injected electrical current is a cardiac pacing pulse configured to initiate a cardiac cycle.

14. The device of claim 12, wherein the injected electrical current is configured such that a cardiac cycle is not initiated in response to injection of the electrical current.

15. The device of claim 12, wherein the current injection, voltage measurement, first impedance value calculation, and second impedance value calculation is repeated on a periodic basis and the assessing pulmonary edema includes assessing a change in edema based on two or more of the calculated impedance values.

16. The device of claim 15, wherein the control module is further designed to assess heart enlargement based on the calculated impedance values.

17. The device of claim 16, wherein relative contributions to impedance changes attributable to pulmonary edema and heart enlargement are determined by solving a system equations using the calculated impedance values and predetermined coefficients.

18. A method of monitoring pulmonary edema in a human being, the method comprising: injecting an electrical current between a first electrode located in or around a heart and a housing of a medical device implanted in a chest region; measuring a first voltage potential between a second electrode and a third electrode, at least one of the second electrode and the third electrode in a superior vena cava, the voltage potential created by the electrical current; measuring a second voltage potential between a fourth electrode in the vena cava and either the second electrode or the third electrode; and assessing pulmonary edema based on (A) a first impedance value calculated from the electrical current and the voltage potential and a stored edema threshold impedance value and (B) a second impedance value calculated based on the electrical current and the second voltage potential.

19. The method of claim 18, wherein the second electrode is in the superior vena cava and the third electrode is not in the superior vena cava, and wherein the third electrode is at the housing of the medical device or at the header of the medical device.

20. The method of claim 18, wherein each of the second electrode and the third electrode is in the superior vena cava and is located on a first lead, and wherein the first electrode is located on a second lead, different from the first lead.

* * * * *

UNITED STATES PATENT AND TRADEMARK OFFICE
CERTIFICATE OF CORRECTION

PATENT NO. : 8,731,653 B2
APPLICATION NO. : 13/122664
DATED : May 20, 2014
INVENTOR(S) : Robert Patterson and Fei Yang Page 1 of 1

It is certified that error appears in the above-identified patent and that said Letters Patent is hereby corrected as shown below:

In the Claims:

Column 16, Line 26, Claim 10, please delete "fight" and insert -- right --, therefor.

Signed and Sealed this
Fifth Day of August, 2014

Michelle K. Lee
*Deputy Director of the United States Patent and Trademark Office*